(12) United States Patent
Locke et al.

(10) Patent No.: US 10,471,190 B2
(45) Date of Patent: Nov. 12, 2019

(54) WOUND DEBRIDEMENT BY IRRIGATION WITH ULTRASONICALLY ACTIVATED MICROBUBBLES

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 611 days.

(21) Appl. No.: 15/147,666

(22) Filed: May 5, 2016

(65) Prior Publication Data
US 2016/0325028 A1 Nov. 10, 2016

Related U.S. Application Data

(60) Provisional application No. 62/158,630, filed on May 8, 2015.

(51) Int. Cl.
*A61M 35/00* (2006.01)
*A61M 1/00* (2006.01)
(Continued)

(52) U.S. Cl.
CPC .......... *A61M 1/0088* (2013.01); *A61B 17/32* (2013.01); *A61B 17/3203* (2013.01); *A61F 13/00068* (2013.01); *A61M 1/0084* (2013.01); *A61M 3/0229* (2013.01); *A61B 2017/22008* (2013.01); *A61B 2017/22089* (2013.01); *A61B 2017/320008* (2013.01); *A61B 2017/32032* (2013.01);
(Continued)

(58) Field of Classification Search
CPC .......... A61M 35/00; A61M 1/00; A61M 3/00; A61M 31/00; A61F 13/00; A61F 13/02; A61F 8/44
See application file for complete search history.

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

PCT International Search Report and Written Opinion corresponding to PCT/US2016/031070 dated Jul. 14, 2016.

(Continued)

*Primary Examiner* — Tatyana Zalukaeva
*Assistant Examiner* — Ilya Y Treyger

(57) ABSTRACT

A treatment system for debriding a treatment area of a tissue site and applying negative pressure is disclosed. In some embodiments, the treatment system may include an ultrasonic bubble generator fluidly coupled to a negative-pressure source, fluid source, and a dressing. Fluid may be drawn from the fluid source to the ultrasonic bubble generator, whereby micro-bubbles and ultrasonic waves may be generated in the fluid before the fluid is instilled to the dressing.

21 Claims, 2 Drawing Sheets

(51) Int. Cl.
  *A61F 13/00* (2006.01)
  *A61B 17/3203* (2006.01)
  *A61B 17/32* (2006.01)
  *A61M 3/02* (2006.01)
  *A61M 3/00* (2006.01)
  *A61F 13/02* (2006.01)
  *A61B 17/22* (2006.01)
  *A61L 2/10* (2006.01)

(52) U.S. Cl.
  CPC ............ *A61B 2017/320084* (2013.01); *A61F 2013/0017* (2013.01); *A61F 2013/0028* (2013.01); *A61F 2013/00174* (2013.01); *A61F 2013/00357* (2013.01); *A61F 2013/00582* (2013.01); *A61L 2/10* (2013.01); *A61L 2202/11* (2013.01); *A61M 3/0275* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,916,296 B2 * | 7/2005 | Soring ............ A61B 17/22004 310/311 |
| 8,075,503 B2 * | 12/2011 | Jaeb .................. A61N 7/00 600/439 |
| 9,375,352 B2 * | 6/2016 | Robinson ............ A61F 13/0203 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0171675 A1 | 9/2003 | Rosenberg |
| 2007/0055179 A1 | 3/2007 | Deem et al. |
| 2008/0195036 A1 | 8/2008 | Merchant et al. |
| 2008/0281383 A1 * | 11/2008 | Butler .................. A61N 5/0616 607/80 |
| 2010/0057025 A1 | 3/2010 | Aicher |
| 2010/0168689 A1 | 7/2010 | Swain et al. |
| 2012/0123360 A1 | 5/2012 | Locke et al. |
| 2012/0227761 A1 | 9/2012 | Leighton et al. |
| 2015/0196431 A1 * | 7/2015 | Dunn ................ A61F 13/00068 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |

(56) References Cited

FOREIGN PATENT DOCUMENTS

| GB | 2 197 789 A | 6/1988 |
|---|---|---|
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English thereof translation.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P,: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

WOUND DEBRIDEMENT BY IRRIGATION WITH ULTRASONICALLY ACTIVATED MICROBUBBLES

The present invention claims the benefit under 35 U.S.C. § 119(e), of the filing of U.S. Provisional Patent Application Ser. No. 62/158,630, filed May 8, 2015, the disclosure of which is hereby incorporated by reference in its entirety.

TECHNICAL FIELD

The invention set forth in the appended claims relates generally to tissue treatment systems and more particularly, but without limitation, to debridement devices, systems, and methods suitable for debriding a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of a wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that debridement of a tissue site can be highly beneficial for new tissue growth. Debridement may refer to a process for removing dead, damaged, or infected tissue from a tissue site for improving the healing potential of healthy tissue remaining at the tissue site. Several factors may make proper debridement difficult, such as challenging wound locations, immobile patients, and environmental constraints. Further, debridement may often be painful for the patient, and in some circumstances may also require a high level of skill from the caregiver, thereby presenting additional challenges. Additionally, debridement methods that are less painful to patients may be relatively slow processes. Therefore, improvements to debridement devices, systems, and methods that may reduce the amount of time to debride a tissue site as well as reduce the risks of pain for the patient or damage to healthy tissue associated with conventional methodologies may be desirable.

BRIEF SUMMARY

New and useful systems, apparatuses, and methods for debriding a tissue site are set forth in the appended claims. Illustrative embodiments are also provided to enable a person skilled in the art to make and use the claimed subject matter.

In some embodiments, a system for treating a tissue site may include a dressing, a negative-pressure source fluidly coupled to the dressing, a fluid source, and an ultrasonic bubble generator. The ultrasonic bubble generator may be fluidly coupled to the fluid source and to the dressing and may be configured to generate micro-bubbles and ultrasonic waves in a fluid from the fluid source.

In other embodiments, a method for debriding necrotic tissue from a tissue site may include coupling a fluid source to the tissue site, supplying a fluid from the fluid source to an ultrasonic bubble generator, generating micro-bubbles and ultrasonic waves in the fluid with the ultrasonic bubble generator, and delivering the micro-bubbles and ultrasonic waves to the necrotic tissue. The ultrasonic bubble generator may further include an ultra-violet light source. In some embodiments, the method may further include coupling a negative-pressure source to a dressing.

Other aspects, features, and advantages of the illustrative embodiments will become apparent with reference to the drawings and detailed description that follow.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
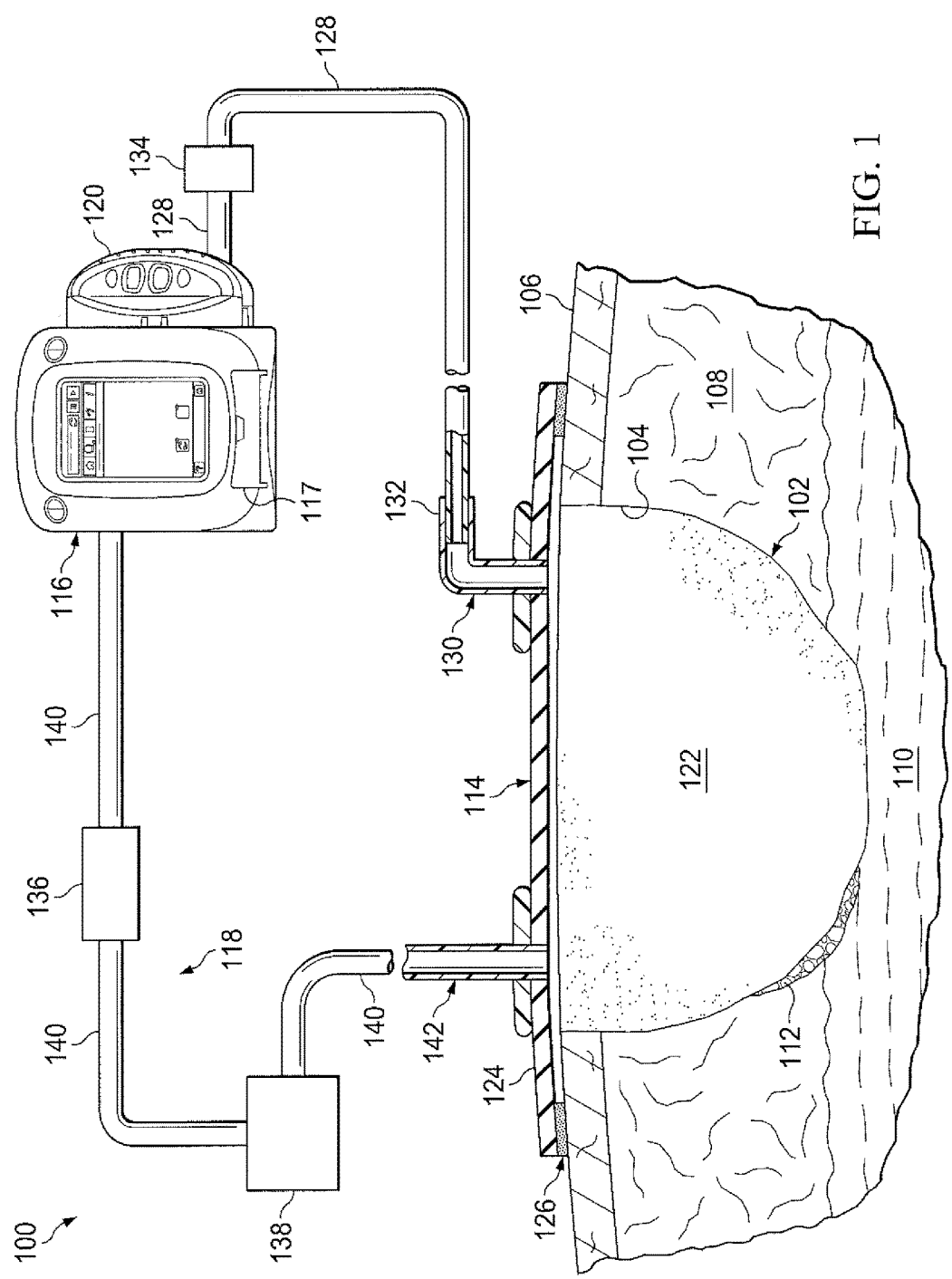
FIG. 1 is a schematic diagram of an example embodiment of negative-pressure therapy system that can deliver ultrasonically-activated micro-bubbles in accordance with this specification.

Referring now primarily to FIG. 1, a therapy system 100 that can provide negative-pressure therapy with instillation of topical treatment solutions for treating a tissue site 102 is presented. The tissue site 102 may include, without limitation, any irregularity with a tissue, such as an open wound, surgical incision, or diseased tissue. The therapy system 100 is presented in the context of a tissue site 102 that includes a wound 104, which is through the epidermis 106, or generally skin, and the dermis 108 and reaching into a hypodermis, or subcutaneous tissue 110. The therapy system 100 may be used to treat a wound of any depth, as well as many different types of wounds including open wounds or other tissue sites. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 102 may include removal of fluids, for example, exudate or ascites.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

As used herein, the terms "debride," "debriding," and "debridement," relate to the act of removing or the removal of undesirable tissue, such as, eschar, necrotic, damaged, infected, contaminated, or adherent tissue, or foreign material from a tissue site. Several methods of debridement may be employed to treat a wound 104 having necrotic tissue 112, including surgical debridement, mechanical debridement, chemical or enzymatic debridement, and autolytic debridement.

However, each of these methods has both advantages and disadvantages. For example, while mechanical debridement is perhaps the fastest method of debridement, it is almost invariably painful or at least submits the patient to a significant level of discomfort. Additionally, mechanical debridement typically requires a high level of skill from the caregiver.

Chemical, or enzymatic, debridement entails the use of chemical enzymes to convert the necrotic tissue to slough. Chemical debridement may be fast-acting and cause minimal damage to healthy tissue if the chemicals are applied properly. However, chemical debridement has disadvantages as well. The process may be expensive and traditional chemical debridement methods and systems, such as low pH systems, may be painful to a patient. Other debriding agents, such as papain, may have other health implications and only have limited usage that is restricted by law. Other agents may be used, such as medical grade honey, but can become quickly mobile in the presence of fluid, such as wound exudate, and an applied negative pressure.

Autolytic debridement, or autolysis, entails the use of the body's own enzymes and white blood cells, along with moisture, to hydrate and liquefy the necrotic tissue 112 and slough. Since autolytic debridement is a naturally occurring process, it is relatively painless and does not risk damage to healthy tissue. Further, autolytic debridement does not require wound fluid to remain in contact with the necrotic tissue 112, and can be facilitated by the use of films, hydrocolloids, and hydrogels. A disadvantage of autolytic debridement is that autolytic debridement is slower than other types of debridement, rendering the wound susceptible to infection.

Thus, there is a need for a debriding process that accelerates, and thereby enhances, the naturally-occurring debridement process without the disadvantages associated with mechanical debridement, while also not using enzymes or other chemicals or drugs. Moreover, it is desirable to have a system and method that allow negative-pressure treatment to occur. As disclosed herein, the therapy system 100 may address these outstanding needs and others. For example, the therapy system 100 may provide a low-pain alternative for enhanced debridement and healing of wounds that can be used in conjunction with negative-pressure treatment.

Referring again to FIG. 1, the wound 104 may include necrotic tissue 112, and in many instances, it may be desirable to remove the necrotic tissue 112 in order to promote healing of the wound 104. The illustrative, non-limiting embodiment shows the therapy system 100 in the context of the wound 104 having a localized, or discrete area, of necrotic tissue 112 within the wound. The therapy system 100 may be used in broader contexts, including with any tissue site having undesirable tissue. Such undesirable tissue may include, necrotic, damaged, infected, contaminated, or adherent tissue, foreign material within the wound 104, and may include a layer of necrotic tissue 112 that covers the entire surface of the wound 104.

The therapy system 100 may include a dressing, a negative-pressure source, a fluid source, and a micro-bubble source. For example, a dressing 114 may be fluidly coupled to a negative-pressure source 116, a fluid source 117, and a micro-bubble subsystem 118, as illustrated in FIG. 1. The therapy system 100 may also include a container for supplying fluid as well as collecting exudates, such as a container 120, coupled to the dressing 114 and to the negative-pressure source 116.

In general, components of the therapy system 100 may be coupled directly or indirectly. For example, the negative-pressure source 116 may be directly coupled to components of the micro-bubble subsystem 118 and the container 120, and indirectly coupled to the dressing 114 through the micro-bubble subsystem 118 and the container 120. In some embodiments, components may be coupled by virtue of physical proximity, being integral to a single structure, or being formed from the same piece of material. Coupling may also include mechanical, thermal, electrical, or chemical coupling (such as a chemical bond) in some contexts.

Components may also be fluidly coupled to each other to provide a path for transferring fluids (i.e., liquid and/or gas) between the components. In some embodiments, for example, components may be fluidly coupled through a tube. A "tube," as used herein, broadly refers to a tube, pipe, hose, conduit, or other fluid conductor with one or more lumina adapted to convey fluid between two ends. Typically, a tube is an elongated, cylindrical structure with some flexibility, but the geometry and rigidity may vary. A fluid conductor may also be integrally molded into a component in some embodiments.

The dressing 114 may be placed within, over, on, or otherwise proximate to the tissue site 102. The dressing 114 may be sealed to tissue near the tissue site 102. For example, the dressing 114 may be sealed to undamaged epidermis peripheral to the tissue site 102. Thus, the dressing 114 can provide a sealed therapeutic environment proximate to the tissue site 102, substantially isolated from the external environment, and the negative-pressure source 116 can reduce the pressure in the sealed therapeutic environment. Negative pressure applied across the tissue site 102 through the dressing 114 in the sealed therapeutic environment can induce macro-strain and micro-strain in the tissue site, as well as remove exudate and other fluid from the tissue site 102, which can be collected in the container 120.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art.

In general, fluid flows toward lower pressure along a fluid path. Thus, the term "downstream" typically implies something in a fluid path relatively closer to a source of negative pressure or further away from a source of positive pressure; conversely, the term "upstream" implies something relatively further away from a source of negative pressure or closer to a source of positive pressure. Similarly, it may be convenient to describe certain features in terms of fluid "inlet" or "outlet" in such a frame of reference, and the process of reducing pressure may be described illustratively herein as "delivering," "distributing," or "generating" reduced pressure, for example. This orientation is generally presumed for purposes of describing various features and components herein.

"Negative pressure" generally refers to a pressure less than a local ambient pressure, such as the ambient pressure in a local environment external to a sealed therapeutic environment provided by the dressing 114. In many cases, the local ambient pressure may also be the atmospheric pressure at which a tissue site is located. Alternatively, negative pressure may be a pressure less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 116, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The fluid source 117 may be housed within or used in conjunction with other components to facilitate movement of a fluid. The fluid source 117 may be a fluid pump, for example a peristaltic pump. Alternatively, in some embodiments, the fluid source 117 may be a fluid reservoir, which may store and deliver fluid. In any embodiment, the fluid source 117, such as a fluid pump or a fluid reservoir, may include a container, such as a canister, pouch, or other storage component. In some embodiments the fluid source 117 may be a fluid pump that helps supply the micro-bubble subsystem 118 with the fluid that may ultimately be delivered to a tissue site.

The dressing 114 may include a manifold 122 and a drape 124. The dressing 114 may also include an attachment device 126 that affixes the drape 124 to the epidermis 106 of the patient. The drape 124 may also include an adhesive surface that seals directly against the epidermis 106 of the patient without the need for an attachment device. The manifold 122 may be positioned between a tissue-facing surface of the drape 124 and the tissue site 102.

The manifold 122 may generally include any substance or structure providing a plurality of pathways adapted to collect or distribute fluid across a tissue site. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate distributing fluid across a tissue site.

In some illustrative embodiments, the pathways of a manifold may be interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and fluid pathways. In some illustrative embodiments, a manifold may be a porous foam material having interconnected cells or pores adapted to distribute negative pressure across a tissue site. The foam material may be either hydrophobic or hydrophilic. The pore size of a foam material may vary according to needs of a prescribed therapy. For example, in some embodiments, the manifold 122 may include a wound filler, which may be a foam having a large pore size or may be a perforated felted foam. The pores or perforations of the wound filler may be in the range of 3-7 millimeters (mm) in diameter, and preferably about 5 mm in diameter. The tensile strength of the manifold 122 may also vary according to needs of a prescribed therapy. For example, the tensile strength of a foam may be increased for instillation of topical treatment solutions. In one non-limiting example, the manifold 122 may be an open-cell, reticulated polyurethane foam such as GranuFoam® dressing available from Kinetic Concepts, Inc. of San Antonio, Tex.; in other embodiments the manifold 122 may be an open-cell, reticulated polyurethane foam such as a VeraFlo® foam, also available from Kinetic Concepts, Inc., of San Antonio, Tex.

In an example in which the manifold 122 may be made from a hydrophilic material, the manifold 122 may also wick fluid away from a tissue site, while continuing to distribute negative pressure to the tissue site. The wicking properties of the manifold 122 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the manifold 122 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 122 may further serve as a scaffold for new cell-growth, or a scaffold material may be used in conjunction with the manifold 122 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the drape 124 may provide a bacterial barrier and protection from physical trauma. The drape 124 may also be constructed from a material that can reduce evaporative losses and provide a fluid seal between two components or two environments, such as between a therapeutic environment and a local external environment. The drape 124 may be, for example, an elastomeric film or membrane that can provide a seal adequate to maintain a negative pressure at a tissue site for a given negative-pressure source. In some example embodiments, the drape 124 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

In some embodiments, an attachment device 126 may be used to attach the drape 124 to an attachment surface, such as undamaged epidermis, a gasket, or another cover. The attachment device 126 may take many forms. For example, an attachment device may be a medically-acceptable, pressure-sensitive adhesive that extends about a periphery, a portion, or the entire drape 124. In some embodiments, for example, some or all of the drape 124 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The negative pressure provided by the negative-pressure source 116 may be delivered through a conduit 128 to a negative-pressure interface 130, which may be an elbow port 132. In one illustrative embodiment, the negative-pressure interface 130 is a T.R.A.C.® Pad or Sensa T.R.A.C.® Pad available from KCI of San Antonio, Tex. The negative-pressure interface 130 allows the negative pressure to be delivered to the drape 124 and realized within an interior portion of the drape 124 and the manifold 122. In this illustrative, non-limiting embodiment, the elbow port 132 extends through the drape 124 to the manifold 122, but numerous arrangements are possible.

The container 120 is representative of a container, canister, pouch, or other storage component, which can be used to manage exudate and other fluid withdrawn from a tissue site. In many environments, a rigid container may be preferred or required for collecting, storing, and disposing of fluid. In some preferred embodiments, the container 120 may be positioned in fluid communication between the negative-pressure source 116 and the dressing 114 to collect fluid drawn from a tissue site. The container 120 may also include features that enable filtering of the effluent that is withdrawn from the dressing 114 and tissue site 102. In some embodiments, the container 120 may attach to the negative-pressure source 116, as illustrated in FIG. 1.

The container 120 may include multiple ports and connection interfaces for integration with the negative-pressure source 116, the fluid source 117, and the other components of the therapy system 100. For example, the container 120 may have two outlets, one of which may be for fluidly connecting the container 120 to the fluid source 117, and the second of which may be for fluidly connecting the container 120 to the negative-pressure source 116.

The micro-bubble subsystem 118 may include a UV light sterilizer 136 and an ultrasonic bubble generator 138. The UV light sterilizer 136 may be positioned in fluid connection between the negative-pressure source 116 and the ultrasonic bubble generator 138. In some embodiments, the micro-bubble subsystem 118 may be fluidly connected to the negative-pressure source 116 and the dressing 114 by the supply conduit 140. In some embodiments, the micro-bubble subsystem 118 may be in close physical proximity to the dressing 114, or optionally incorporated as part of the dressing 114. In other embodiments, some or all of the components of the micro-bubble subsystem 118 may be incorporated within the negative-pressure source 116.

As fluid is moved from the negative-pressure source 116 through the supply conduit 140 to the ultrasonic bubble generator 138, the fluid may pass through the UV light sterilizer 136. The UV light sterilizer 136 may contain a UV light source, which may dose the fluid passing through the UV light sterilizer 136 with UV light to kill any pathogens that may be in the fluid. Once the fluid has passed through the UV light sterilizer 136, the fluid may be delivered to the ultrasonic bubble generator 138 through supply conduit 140.

Figure 2:
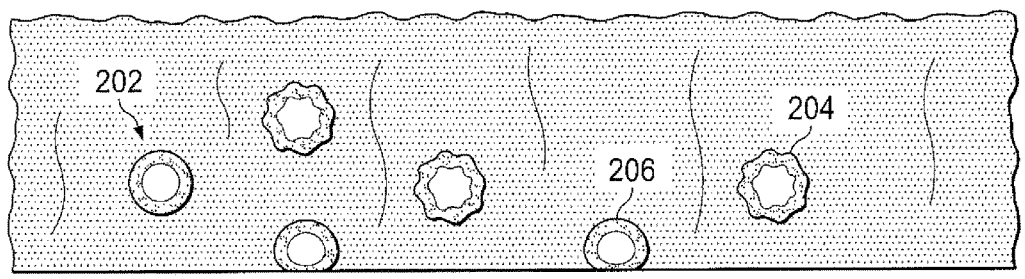
FIG. 2 is a perspective view illustrating additional details that may be associated with some example embodiments of the negative-pressure therapy system of FIG. 1.

The ultrasonic bubble generator 138 may function to generate both micro-bubbles and an ultrasonic waveform in a fluid. For example, the ultrasonic bubble generator 138 may be an apparatus for generating an output flow of liquid, including an acoustic transducer for introducing acoustic energy into the liquid and a gas bubble generator for generating gas bubbles within the liquid, as described in U.S. Patent Application Publication No. US 2012/0227761 A1, which is hereby incorporated by reference in its entirety. As illustrated in FIG. 1, fluid may be delivered from the UV light sterilizer 136 through supply conduit 140 to the ultrasonic bubble generator 138. As the fluid passes through the ultrasonic bubble generator 138, the ultrasonic bubble generator 138 may generate and inject gas bubbles within the fluid. While the micro-bubbles may be generated in a range of sizes, the micro-bubbles may typically be approximately 15-200 micrometers (μm) in diameter. The ultrasonic bubble generator 138 may then generate an ultrasonic waveform that may be conducted through the fluid as it flows through the ultrasonic bubble generator 138. In some embodiments, the ultrasonic bubble generator 138 may include a transducer that emits acoustic energy. The acoustic energy may be emitted as intermittent pulses. Referring also to FIG. 2, as micro-bubbles 202 are hit by the ultrasonic waves, the micro-bubbles may undergo significant deformation which may manifest itself as a ripple 204 at the gas/liquid interface. As a result of this ripple, the micro-bubble can exert a scrubbing action on surfaces it touches as the micro-bubble 206 is deformed, and the turbulence formed around the micro-bubble may also cause the micro-bubble to be drawn to surfaces and into cracks and crevices, such as deformities at a tissue site.

In some embodiments, the manifold 122 may be tailored to cause minimal attenuation of the ultrasonic energy generated by the micro-bubble source 118. For example, the manifold 122 may be largely constructed from polymers that are hydrophilic, which may contain water or be configured to absorb water. Such hydrophilic polymers may include poly hydroxy ethyl methacrylate, copolymer of N-vinyl pyrrolidone and 2-hydroxy ethyl methacrylate, terpolymer based on glycerol methacrylate, copolymer of N-vinyl pyrrolidone and methyl methacrylate, as well as polymethyl methacrylate (PMMA). Additionally, the manifold 122 may be constructed from hydrophilic polyurethane polymers, such as TECOPHILIC hydrophilic polyurethanes available from The Lubrizol Corp. of Wickliffe, Ohio, which in extrusion grade formulations, may absorb water up to 100% of the weight of dry resin (900% of weight of dry resin for hydrogel grades) while retaining structural integrity. In some embodiments, the manifold 122 may be formed from one of the hydrophilic polymers listed above into a porous or foamed structure with pores measuring approximately 5-10 mm in diameter, which may minimize the number of struts that could interfere with the passage of bubbles. In other embodiments, the manifold 122 may be formed from one of the hydrophilic polymers formed into a perforated sheet having protrusions on one side. In some instances, the protrusions may be spaced about 5-10 mm apart from each other, and may be hemispherical or polygonal in shape. The protrusions may act as spacers between the wound 104 and the drape 124.

The therapy system 100 presented in FIG. 1 may also include a second interface, such as fluid-delivery interface 142. The fluid-delivery interface 142 may be fluidly coupled to the dressing 114 and may pass through a hole cut in the drape 124. The hole cut in the drape for the fluid-delivery interface 142 may be separated as far apart as possible from the location or other hole cut in the drape through which the negative-pressure interface 130 may pass. The fluid-delivery interface 142 may allow for a fluid to be delivered by the therapy system 100 through the drape 124 and to the manifold 122 and the tissue site 102.

In some embodiments, the fluid-delivery interface 142 may include an inlet pad. The inlet pad may be a non-dampening material or a material that is not sound-absorbing. In some embodiments, the inlet pad may be an elastomer. For example, the inlet pad may be an elastic polymer, such as polyurethane, thermoplastic elastomers, polyether block amide (PEBAX), polyisoprene, polychloroprene, chlorosulphonated polythene, and polyisobutylene, blends and copolymers.

The composition of the fluid may vary according to a prescribed therapy, but examples of solutions that may be suitable for some prescriptions include a saline solution with a low level of surfactant, such as ≤0.1%, and more typically 0.015%. Such surfactants may include Pluronic F68, polyolefin oxides, and polyolefin glycols. By including a surfactant in the fluid, the generated micro-bubbles may be preserved for a longer duration as they travel from the ultrasonic bubble generator 138 to the tissue site 102.

The therapy system 100 may also include a particulate filter 134, which may be positioned in fluid communication between the container 120 and/or the negative-pressure source 116 and the dressing 114. The particulate filter 134 may function to remove particulate matter from the effluent that has circulated through the dressing 114. For example, in the embodiment pictured in FIG. 1, fluid delivered to the dressing 114 and to the tissue site 102 may be drawn out of the dressing 114 through the negative-pressure interface 130 and transported through negative-pressure conduit 128 to the particulate filter 134. The fluid may be filtered to remove particulate matter in the particulate filter 134, before being recollected in the container 120.

In operation, the negative-pressure source 116 may pump fluid, such as a saline solution through the supply conduit 140 to a UV light sterilization unit, such as UV light sterilizer 136. Once the fluid has passed through the UV light sterilizer 136, the fluid may continue through supply conduit 140 to the ultrasonic bubble generator 138, where micro-bubbles may be generated in the fluid, followed by the fluid and micro-bubbles being activated by ultrasonic energy applied by the ultrasonic bubble generator 138. The activated fluid may then pass through the fluid-delivery interface 142 and into the dressing 114. The activated fluid may then pass through the manifold 122 and reach the wound 104, where the activated fluid may debride necrotic tissue 112.

Following the debridement of the necrotic tissue 112 by the activated fluid, the remaining effluent may be drawn out of the dressing 114 by negative pressure applied to the dressing 114 and tissue site 102 by the negative-pressure source 116. For example, the effluent may be drawn from the wound 104, through the manifold 122, and out of the dressing 114 through the negative-pressure interface 130. The effluent may then pass through negative-pressure conduit 128 to the particulate filter 134, where particulate matter may be filtered out of the effluent. The filtered fluid may then be collected by the container 120 before being recirculated by the negative-pressure source 116 through the UV light sterilizer 136 and ultrasonic bubble generator 138 to the wound 104.

The systems, apparatuses, and methods described herein may provide significant advantages. For example, a therapy system described above may provide a low-pain, clean method to achieve an alternative form of mechanical debridement. The therapy system can keep a wound enclosed, thus reducing the possible risk of infection, and can also store any particulate matter in a convenient location that may be easily disposed. The therapy system may also reduce the risk of contaminating the environment external to a wound with potentially infectious matter, and can also keep odors contained.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for treating a tissue site, comprising:
   a dressing for placing on the tissue site;
   a negative-pressure source fluidly coupled to the dressing;
   a fluid source; and
   an ultrasonic bubble generator coupled between the fluid source and the dressing, the ultrasonic bubble generator comprising:
      a gas bubble generator configured to inject micro-bubbles in a fluid from the fluid source prior to the fluid entering the dressing, and
      an acoustic transducer configured to transmit ultrasonic waves to the micro-bubbles in the fluid prior to the fluid entering the dressing.

2. The system of claim 1, further comprising an ultra-violet light source configured to generate and treat the fluid with ultra-violet light.

3. The system of claim 1, further comprising a container fluidly coupled to the negative-pressure source and the dressing and configured to collect fluids.

4. The system of claim 1, further comprising a connection interface configured to fluidly connect the negative-pressure source to the dressing.

5. The system of claim 1, further comprising a connection interface configured to deliver the fluid to the dressing.

6. The system of claim 1, wherein the dressing comprises:
   a manifold adapted to be placed proximate to the tissue site; and
   a drape adapted to be placed over the manifold.

7. The system of claim 6, wherein the manifold comprises a perforated felted foam.

8. The system of claim 7, wherein the perforated felted foam comprises perforations in a range of 3-7 millimeters (mm) in diameter.

9. The system of claim 8, wherein the perforations are approximately 5 millimeters (mm) in diameter.

10. The system of claim 6, wherein the manifold comprises a hydrophilic polymer.

11. The system of claim 10, wherein the hydrophilic polymer is a hydrophilic polyurethane polymer.

12. The system of claim 6, wherein the manifold comprises a hydrophilic polymer formed into a porous structure and having perforations in a range of 5-10 millimeters (mm) in diameter.

13. The system of claim 6, wherein the manifold comprises a hydrophilic polymer formed into a perforated sheet having protrusions on a first side.

14. The system of claim 13, wherein the protrusions are spaced apart by a range of 5-10 millimeters (mm).

15. The system of claim 13, wherein the protrusions are hemispherical or polygonal in shape.

16. The system of claim 1, wherein the fluid source comprises a pump.

17. The system of claim 1, wherein the fluid source comprises a reservoir.

18. A method for debriding necrotic tissue from a tissue site, comprising:
   applying a dressing to the tissue site;
   coupling a fluid source to the dressing;
   supplying a fluid from the fluid source to an ultrasonic bubble generator, the ultrasonic bubble generator comprising an acoustic transducer and a gas bubble generator;
   injecting micro-bubbles into the fluid with the gas bubble generator;
   generating ultrasonic waves in the fluid with the acoustic transducer prior to the fluid entering the dressing to deform at least a portion of the micro-bubbles; and
   delivering the fluid with micro-bubbles and ultrasonic waves to the dressing.

19. The method of claim 18, wherein the ultrasonic bubble generator further comprises an ultra-violet light source configured to generate and treat the fluid with ultra-violet light.

20. The method of claim 18, further comprising coupling a negative-pressure source to the dressing.

21. A system for treating a tissue site, comprising:
   a dressing for placing on the tissue site comprising:
      a manifold adapted to be placed proximate the tissue site, and
      a drape adapted to be placed over the manifold;
   a negative-pressure source fluidly coupled to the dressing;
   a fluid source; and
   an ultrasonic bubble generator coupled between the fluid source and the drape, the ultrasonic bubble generator configured to inject bubbles into the fluid and generate ultrasonic waves in the fluid prior to the fluid entering the manifold through the drape.

* * * * *